United States Patent
Boden et al.

(10) Patent No.: US 11,083,516 B2
(45) Date of Patent: Aug. 10, 2021

(54) SYSTEMS AND METHODS FOR MAPPING AND ABLATION IN THE BLADDER

(71) Applicant: Boston Scientific Scimed, Inc., Maple Grove, MN (US)

(72) Inventors: Mark W. Boden, Harrisville, RI (US); Sandra Nagale, Bolton, MA (US); Yitzhak Mendelson, Worcester, MA (US); Glenn Gaudette, Holden, MA (US); Deanna Cavallaro, Medford, MA (US); Tristan Richardson, North Attleboro, MA (US); Tyler Hickey, Eliot, ME (US); Rami Shuraim, Worcester, MA (US); Dervis Goksun, Nicosia (CY)

(73) Assignee: Boston Scientific Scimed, Inc., Maple Grove, MN (US)

( * ) Notice: Subject to any disclaimer, the term of this patent is extended or adjusted under 35 U.S.C. 154(b) by 563 days.

(21) Appl. No.: 15/227,762

(22) Filed: Aug. 3, 2016

(65) Prior Publication Data

US 2017/0035498 A1   Feb. 9, 2017

Related U.S. Application Data

(60) Provisional application No. 62/200,161, filed on Aug. 3, 2015.

(51) Int. Cl.
*A61B 18/14*   (2006.01)
*A61B 18/00*   (2006.01)
*A61B 17/00*   (2006.01)

(52) U.S. Cl.
CPC ............... *A61B 18/1492* (2013.01); *A61B 2017/00022* (2013.01); *A61B 2017/00053* (2013.01);
(Continued)

(58) Field of Classification Search
CPC ........ A61B 18/1492; A61B 2018/0022; A61B 2018/0025; A61B 2018/00261; A61B 2018/00285; A61B 2018/00238; A61B 2018/00517; A61B 2018/00523; A61B 2018/00577; A61B 2018/00654;
(Continued)

(56) References Cited

U.S. PATENT DOCUMENTS 5,865,801 A * 2/1999 Houser ................ A61B 5/036
                                                  600/488
6,409,723 B1 * 6/2002 Edwards ............ A61B 18/1477
                                                  604/20

(Continued)

FOREIGN PATENT DOCUMENTS

CN   103200890 A   7/2013
CN   103987336 A   8/2014
(Continued)

*Primary Examiner* — Eun Hwa Kim
*Assistant Examiner* — Catherine Premraj
(74) *Attorney, Agent, or Firm* — Kacvinsky Daisak Bluni PLLC

(57) ABSTRACT

The present disclosure relates to the field of tissue mapping and ablation. Specifically, the present disclosure relates to expandable medical devices for identifying and treating local anatomical abnormalities within a body lumen. More specifically, the present disclosure relates to systems and methods of focal treatment for overactive bladders.

20 Claims, 5 Drawing Sheets

(52) U.S. Cl.
CPC .......... *A61B 2018/0022* (2013.01); *A61B 2018/0025* (2013.01); *A61B 2018/00166* (2013.01); *A61B 2018/00238* (2013.01); *A61B 2018/00261* (2013.01); *A61B 2018/00517* (2013.01); *A61B 2018/00523* (2013.01); *A61B 2018/00577* (2013.01); *A61B 2018/00654* (2013.01); *A61B 2018/00708* (2013.01); *A61B 2018/00839* (2013.01); *A61B 2018/144* (2013.01); *A61B 2018/1467* (2013.01)

(58) Field of Classification Search
CPC .......... A61B 2018/00708; A61B 2018/00839; A61B 2018/144; A61B 2018/1467; A61B 2017/00022; A61B 2017/00053; A61M 25/10; A61M 25/1011
See application file for complete search history.

(56) References Cited

U.S. PATENT DOCUMENTS

| | | |
|---|---|---|
| 2005/0240249 A1 | 10/2005 | Tu et al. |
| 2011/0184400 A1* | 7/2011 | Pageard ............ A61B 18/02 606/21 |
| 2013/0090649 A1 | 4/2013 | Smith et al. |
| 2015/0105659 A1* | 4/2015 | Salahieh ........... A61M 3/0295 600/435 |
| 2015/0141982 A1 | 5/2015 | Lee |
| 2015/0141987 A1* | 5/2015 | Caplan ............. A61B 18/14 606/41 |

FOREIGN PATENT DOCUMENTS

| | | |
|---|---|---|
| JP | 3072464 | 10/2000 |
| WO | 0069376 A1 | 11/2000 |
| WO | 2005067668 A2 | 7/2005 |
| WO | 2005067791 A1 | 7/2005 |
| WO | 2009001326 A1 | 12/2008 |
| WO | 2010141417 A2 | 12/2010 |

* cited by examiner

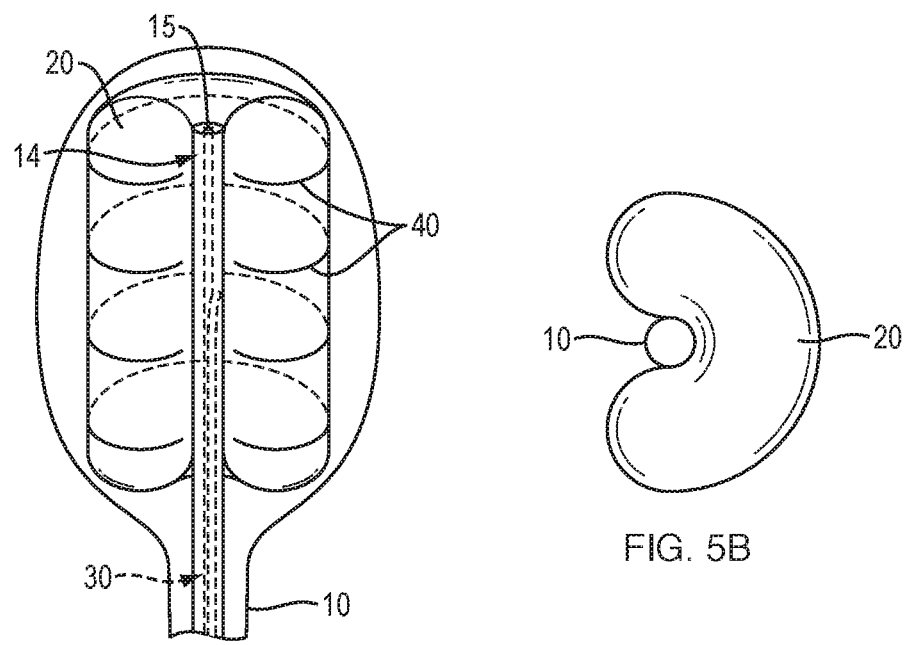
FIG. 5A
FIG. 5B
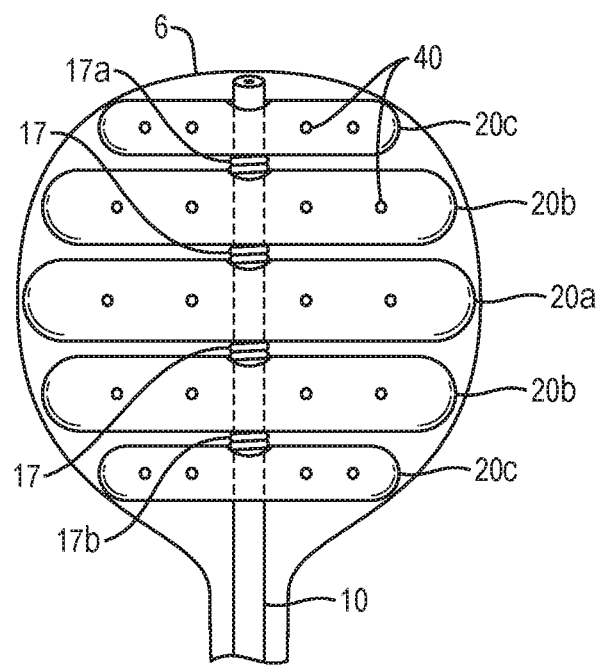
FIG. 6

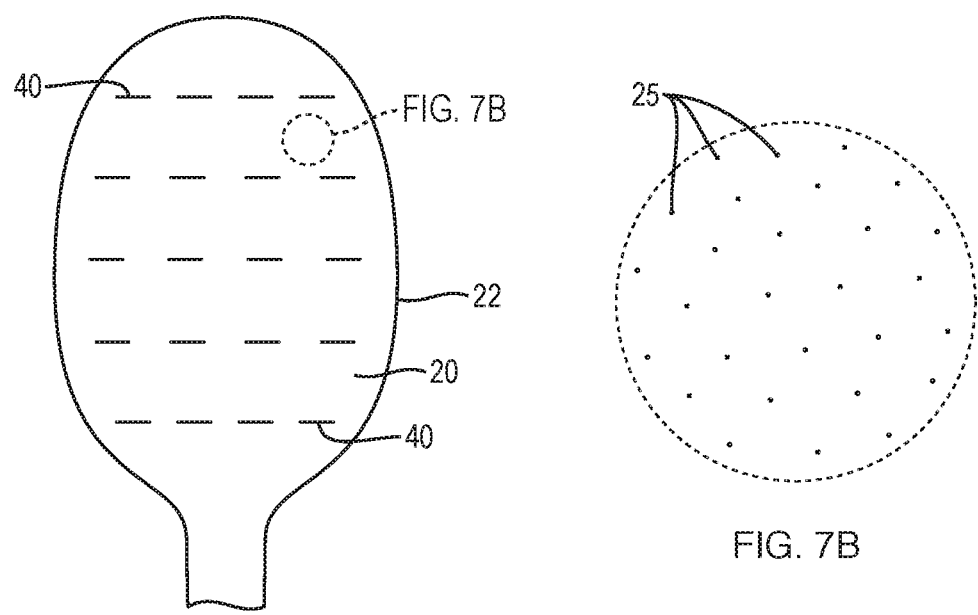
FIG. 7A
FIG. 7B
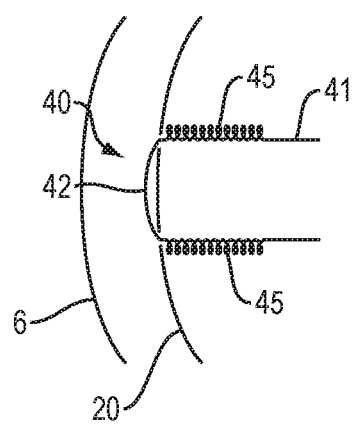
FIG. 8

SYSTEMS AND METHODS FOR MAPPING AND ABLATION IN THE BLADDER

CROSS-REFERENCE TO RELATED APPLICATIONS

This application claims priority to U.S. Provisional Application Ser. No. 62/200,161, filed on Aug. 3, 2015, the entire disclosure of which is herein incorporated by reference.

FIELD

The present disclosure relates to the field of tissue mapping and ablation. Specifically, the present disclosure relates to expandable medical devices for identifying and treating local anatomical abnormalities within body lumens, including the bladder.

BACKGROUND

Overactive bladder is a medical condition that affects more than 50 million people in the United States. Individuals with an overactive bladder typically experience an increase in urge and frequency of urination, and occasionally incontinence. An overactive bladder may result from increased triggering of the sensory pathways involved in normal bladder control. It has been suggested that abnormal bladder activity may result from morphological changes in one or more distinct anatomical areas of the bladder, including the dome, internal sphincter or trigone. For example, localized changes in detrusor muscle morphology resulting from defects at the cellular and multicellular level tend to correlate with pathological changes, e.g., patchy denervation due to increased amounts of connective tissue between muscle bundles, which may contribute to abnormal muscle function on a macroscopic level. These localized defects often manifest as elevated electrical activity within specific tissue regions of the bladder wall. Identifying and treating these localized defects may prevent or eliminate the symptoms of overactive bladder. Current treatments for overactive bladder, such as systemic administration of drugs, nerve stimulation or Botox injections, are applied to the entire bladder rather than specifically targeting local and anatomical abnormalities. Because the therapeutic effect eventually wears off, these treatments often need to be repeated multiple times. Unfortunately, overtreatment may lead to urinary retention that requires self-catheterization to void the bladder.

The transient nature of these systemic treatments may be addressed by mapping the bladder wall to identify where local bladder abnormalities originate and then specifically targeting therapeutic treatment to those areas. Currently available bladder mapping devices do not conform to the shape of the bladder and cannot reliably establish and/or maintain contact between each of the electrodes and the bladder wall. Proper positioning of the electrodes may be achieved by attaching the electrodes to the surface of a balloon, as described by Drake et al. (BJU International 2005, vol. 95, p. 1002). However, the asymmetric shape of the bladder, along with individual variations in size and shape between patients, makes it difficult for a single balloon to establish and maintain contact with the bladder wall.

There is a continued need for systems and methods for identifying local bladder abnormalities and specifically targeting therapeutic treatments to those areas in a minimally invasive manner. Such treatments may provide a permanent therapeutic effect without increasing the duration of the medical procedure.

SUMMARY

Particular embodiments of the disclosure are described in the Summary and Detailed Description of the Preferred Embodiments, below. Although the disclosure has been described in connection with specific embodiments, it should be understood that the disclosure as claimed should not be unduly limited to such specific embodiments.

The present disclosure relates generally to electrode-bearing mapping and ablation systems that provide enhanced electrical connection with the bladder wall, while at the same time reducing or eliminating artifactual electrical measurements resulting from tissue irritation.

In one aspect, the present disclosure relates to a medical device, comprising: a catheter comprising a proximal end, a distal end and a lumen extending therebetween; a plurality of balloons disposed proximate the distal end of the catheter; a plurality of tubes traversing at least a portion of the catheter lumen, wherein a first end of each of the plurality of tubes is fluidly connected to a different one of the plurality of balloons; and a plurality of electrodes carried about (i.e., "arranged on" or "attached to" etc.) a surface of each of the plurality of balloons. The balloons may include a compliant polymer selected from the group consisting of silicone rubbers, polyurethanes, butyl rubbers, latexes, styrene-isobutylene-styrene block copolymers and EPDM, or a non-compliant polymer selected from PEBAX, PET, PEN, PBT, PEEK, Hytrel, polyurethane and nylon. Each of the plurality of balloons may be configured to move between a collapsed configuration and an expanded configuration. A second end of each of the plurality of tubes may be in fluid communication with a fluid source, such that each balloon moves from a collapsed configuration to an expanded configuration by flowing a fluid from the fluid source into the lumen of the balloon. Each of the plurality of electrodes may contact a wall of the body lumen when the balloons are in the expanded configuration. Each of the plurality of balloons may be spaced along a longitudinal axis of the catheter. For example, the plurality of balloons may comprise a first tier balloon, a second tier balloon and a third tier balloon, wherein the second tier balloon is disposed between the first tier balloon and the third tier balloon. A volume of each of the first, second and third tier balloons may be substantially the same when in the expanded configuration. Alternatively, a volume of the first tier balloon in the expanded configuration may exceed a volume of the second tier balloon in the expanded configuration, and a volume of the second tier balloon in the expanded configuration may exceed a volume of the third tier balloon in the expanded configuration. Similarly, a volume of the second tier balloon in the expanded configuration may exceed a volume of both the first tier balloon in the expanded configuration and the third tier balloon when in the expanded configuration. The maximum volume of a second tier balloon may be at least 5% to 50% greater than the volume of a third tier balloon, and the maximum volume of a first tier balloon may be at least 5% to 50% greater than the volume of a second tier balloon. Alternatively, the maximum volume of a second tier balloon may be at least 100% greater than the volume of a third tier balloon, and the maximum volume of a first tier balloon may be at least 100% greater than the volume of a second tier balloon. Each of the plurality of balloons may include incrementally different volumes depending on their location along the distal end of the catheter, thereby reducing the profile (i.e., diameter) of the tiered balloon catheter when in the collapsed configuration. Each of the plurality of balloons may substantially disc shaped. Each of the plurality of balloons may have a maximum volume of at most about 50 ml, at most about 100 ml, at most about 150 ml, at most about 200 ml, at most about 250 ml, at most about 300 ml and at most about 350 ml. Each of the plurality of balloons may be slidable along the distal end of the catheter. Each of the plurality of balloons may be biased from (i.e., "spaced from," spaced apart from" or "separated from") an adjacent balloon by a spring (i.e., "spacing element") disposed about the catheter. The spring(s) may be slidably disposed about the catheter to maintain a space between the balloons of each tier. The top (i.e., most distal) and bottom (i.e., most proximal) springs may be attached to connecting guides that allow the position of the tiered balloons to be adjusted along the length of the catheter. The connecting guide attached to the top spring may be pulled proximally (i.e., toward the bladder neck) to adjust the balloons proximally, while the connecting guide attached to the bottom spring may be pushed distally (i.e., toward the bladder dome) to adjust the balloons distally. The plurality of balloons may be positioned around a longitudinal axis of the catheter. Each of the plurality of balloons may comprise an elongate longitudinal cross-section. Each of the plurality of balloons may comprise an elongate longitudinal cross-section selected from an elliptical or partially elliptical cross-section, or an obround or partially obround cross-section. The plurality of balloons may be spaced at equal angles of rotation around the longitudinal axis of the catheter. Two balloons may be spaced from one another by 180° of rotation; three balloons may be spaced from one another by 120° of rotation; four balloons may be spaced from one another by 90° of rotation; five balloons may be spaced from one another by 72° of rotation; and six balloons may be spaced apart from one another by 60° of rotation. The first ends of a plurality of conducting wires may be electrically coupled to a different one of the plurality of electrodes. The second ends of the plurality of conducting wires may be electrically coupled to an ablation energy source. The ablation energy source may include a radio frequency (RF) generator. The second end of each of the plurality of conducting wires may be electrically coupled to an electrical activity processing system. The electrical activity processing system may be configured to measure intrinsic electrical activity. Each of the plurality electrodes may be configured to serves as one or more of the following: sensing electrode, mapping electrode, stimulating electrode and/or ablation electrode.

Each of the plurality of balloons may include a plurality of electrodes disposed equidistantly about its outer surface. Each of the plurality of electrodes may be coupled to an electrically conductive wire for performing mapping and ablation functions. The present disclosure is not limited to the number or arrangement of electrodes on the outer surface of each balloon. Any number of electrodes may be disposed about the outer surface of each balloon of the tiered balloon catheter. For example, there may be one, two, three, four, five, six, seven, eight, nine, ten, eleven, twelve, sixteen, twenty, twenty-four, or more electrodes. The electrodes may be arranged in a ring patter, spiral pattern or vertical pattern, as are known in the art. In addition or alternatively, the electrodes may be arranged randomly or in an ordered fashion, for example they may be more densely distributed in the area around bladder neck and less densely distributed in the dome.

The electrodes may include a variety of designs for mapping and ablating the tissues of the bladder wall. The electrode may include a wire that passes through small holes in the balloon surface to form a loop exposed to the outside of the balloon for contact with the bladder wall. The remaining wire may be formed into a shape memorized (e.g., heat trained) coil within the balloon interior, such that the wire may uncoil and recoil as the balloon moves between the expanded and collapsed configurations. Alternatively, the electrode may include a wire in the shape of a coiled ring that wraps around the external surface of the balloon and feeds directly into the lumen of the catheter, thereby eliminating the need for the wire to pass through the balloon surface. Slack provided to the portion of the wire within the lumen of the catheter may allow the electrode to uncoil and recoil as the balloon moves between the expanded and collapsed configurations. Alternatively, the electrode may be a "plunge electrode" that includes a wire formed in the shape of a heat trained coil within the balloon interior that leads to a single point that plugs a small hole in the balloon. The pointed end of the electrode may extend beyond the outer surface of the balloon to contact (i.e., plunge into) the tissues of the bladder wall (e.g., by forming a pressure indentation in the bladder wall or penetrating the bladder wall), thereby maintaining contact with the bladder wall. Alternatively, the electrode may include a single wire that curls around one-half of the outer surface of the balloon such that the distal end of the wire is positioned at a middle portion of the balloon. The wire may feed out of the lumen of the catheter and may be trained in a half-circle formation. As the balloon moves between the expanded and collapsed configurations, the wire may have sufficient space to freely move within the lumen of the catheter. The electrode at the end of the wire may, for example, rest laterally against the outer surface of the balloon, or be shaped as a plunge-type electrode that pushes against or penetrates a tissue of the bladder wall 6.

In another aspect, the present disclosure relates to a medical device, comprising: a catheter comprising a proximal end, a distal end and a lumen extending therebetween; a balloon disposed about a portion of a longitudinal axis of the catheter proximate the distal end of the catheter; a tube traversing at least a portion of the catheter lumen, wherein a first end of the tube is fluidly connected to the balloon; and a plurality of electrodes carried about a surface of the balloon. The balloon may extend around the longitudinal axis by an amount ranging from 90° to 270°. The balloon may comprise an elongate longitudinal cross-section. For example, the elongate cross-section may extend around a longitudinal axis of the catheter by an amount ranging from 90° to 270°. Alternatively, the balloon may comprise an elongate longitudinal cross-section selected from an elliptical or partially elliptical cross-section, or an obround or partially obround cross-section.

In another aspect, the present disclosure relates to a medical device, comprising: a catheter comprising a proximal end, a distal end and a lumen extending therebetween; a balloon disposed proximate the distal end of the catheter, wherein at least a portion of the balloon is fluid permeable; a tube traversing at least a portion of the catheter lumen, wherein a first end of the tube is fluidly connected to the balloon; and a plurality of electrodes carried about a surface of the balloon.

In another aspect, the present disclosure relates to a method, comprising: introducing a medical device into a body lumen, wherein the medical device includes: a catheter comprising a proximal end, a distal end and a lumen extending therebetween; a plurality of balloons disposed proximate the distal end of the catheter; a plurality of tubes traversing at least a portion of the catheter lumen, wherein a first end of each of the plurality of tubes is fluidly connected to a different one of the plurality of balloons; and a plurality of electrodes carried about a surface of each of the plurality of balloons; moving at least one of the plurality of balloons from a collapsed configuration to an expanded configuration such that the electrodes carried about the surface of the balloon contact a tissue of the body lumen; measuring electrical activity within the tissue of the body lumen in contact with each of the electrodes; identifying each electrode that detected an elevated electrical activity within the tissue of the body lumen; and applying electrical energy to each electrode that identified elevated electrical activity. The body lumen may be the lumen of a bladder. Applying the electrical energy may reduce the elevated electrical activity within the tissue of the body lumen, thereby reducing at least one symptom of an overactive bladder.

In another aspect, the present disclosure relates to a method, comprising: introducing a medical device into a body lumen, wherein the medical device includes: a catheter comprising a proximal end, a distal end and a lumen extending therebetween; a balloon disposed about a portion of a longitudinal axis of the catheter proximate the distal end of the catheter; a tube traversing at least a portion of the catheter lumen, wherein a first end of the tube is fluidly connected to the balloon; and a plurality of electrodes carried about a surface of the balloon; moving the balloon from a collapsed configuration to an expanded configuration such that the electrodes carried about the surface of the balloon contact a tissue of the body lumen; measuring electrical activity within the tissue of the body lumen in contact with each of the electrodes; identifying each electrode that detected an elevated electrical activity within the tissue of the body lumen; and applying electrical energy to each electrode that identified elevated electrical activity.

In another aspect, the present disclosure relates to a method, comprising: introducing a medical device into a body lumen, wherein the medical device includes: a catheter comprising a proximal end, a distal end and a lumen extending therebetween; a balloon disposed proximate the distal end of the catheter, wherein at least a portion of the balloon is fluid permeable; a tube traversing at least a portion of the catheter lumen, wherein a first end of the tube is fluidly connected to the balloon; and a plurality of electrodes carried about a surface of the balloon; moving the balloon from a collapsed configuration to an expanded configuration such that the electrodes carried about the surface of the balloon contact a tissue of the body lumen; measuring electrical activity within the tissue of the body lumen in contact with each of the electrodes; identifying each electrode that detected an elevated electrical activity within the tissue of the body lumen; and applying electrical energy to each electrode that identified elevated electrical activity.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures:

FIG. 5A is a side view of an asymmetric balloon catheter, according to another embodiment of the present disclosure.

FIG. 5B is a cross-sectional view of the asymmetric balloon catheter of FIG. 5A.

FIG. 6 is a side view of a sliding balloon catheter, according to another embodiment of the present disclosure.

FIG. 7A is a side view of a weeping balloon catheter, according to yet another embodiment of the present disclosure.

FIG. 7B is a magnified view of the balloon surface of FIG. 7A depicting pores that allow fluid to seep through the wall of the balloon to hydrate the tissues of the bladder wall.

FIG. 8 is a side view of an exposed electrode, according to one embodiment of the present disclosure.

It is noted that the drawings are intended to depict only typical or exemplary embodiments of the disclosure. It is further noted that the drawings are not necessarily to scale. Accordingly, the drawings should not be considered as limiting the scope of the disclosure. The disclosure will now be described in greater detail with reference to the accompanying drawings.

DETAILED DESCRIPTION OF THE PREFERRED EMBODIMENTS

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to systems and methods for mapping and ablating overactive tissue(s) within the bladder, it should be appreciated that the present disclosure may be applicable to mapping and ablating a variety of organs, including, for example, the gastrointestinal (GI) tract, stomach (e.g., irritable bowel disease, cancer, obesity etc.), uterus (e.g., fibroids, uterine bleeding etc.), esophagus and vascular system.

As used herein, the term "distal" refers to the end farthest away from a medical professional when introducing a device into a patient, while the term "proximal" refers to the end closest to the medical professional when introducing a device into a patient.

As used herein, "expandable" or "expanded" refers to an increase in diameter, as compared to the diameter in a "collapsible" or "collapsed" configuration. As used herein, "diameter" refers to the distance of a straight line extending between two points and does not necessarily indicate a particular shape.

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

Figure 1:
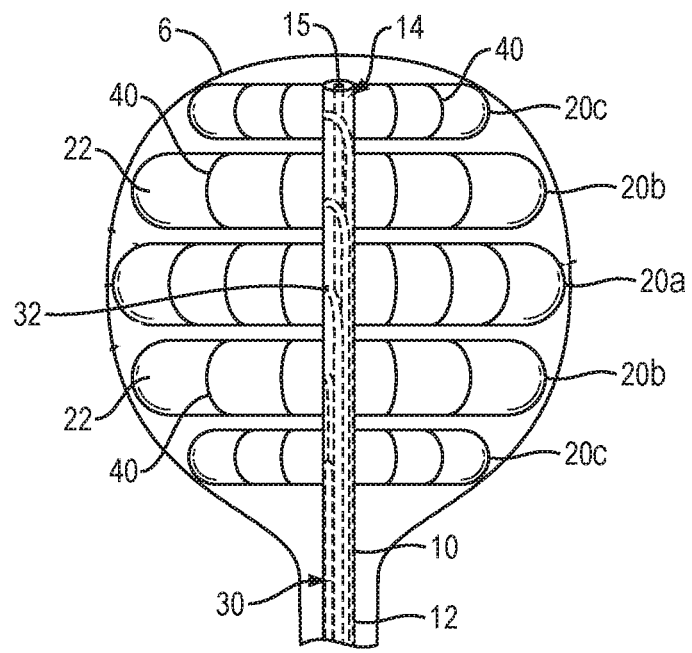
FIG. 1 is a side view of a tiered balloon catheter, according to an embodiment of the present disclosure.

FIG. 1 depicts a schematic side view of a medical device that includes a central catheter 10 having proximal end 12, a distal end 14 and a lumen 15 extending therebetween. A plurality of inflatable balloons 20a-c are stacked along the distal end 14 of the catheter 10 in a tiered or layered configuration, with a plurality of electrodes 40 carried about the outer surface 22 of each balloon 20. Although the embodiment depicted in FIG. 1 includes five balloons stacked along the distal end of the catheter, it will be appreciated that the present disclosure may include fewer or greater than five balloons. A plurality of tubes 30 traverse at least a portion of the catheter lumen 15, with the first end 32 of each tube fluidly connected to a different one of the plurality of balloons 20 and the second end (not shown) of each tube connected to a fluid source (not shown). Each of the balloons is configured to move from a collapsed (i.e., deflated) configuration to an expanded (i.e., inflated) configuration independent of the other balloons by flowing a fluid from the fluid source into the balloon interior region 24 through its respective tube. The fluid may include a pressurized liquid or gas. Similarly, each balloon is configured to move from an expanded configuration to a collapsed configuration independent of the other balloon(s) by flowing the fluid from the interior region of each expanded balloon back into the fluid source through its respective tube. The volume of each balloon may be adjusted by introducing additional fluid, or removing fluid, as necessary to position and maintain the electrodes 40 on the outer surface of each balloon in firm contact with the tissues of the bladder wall 6 during the mapping and ablation process, as discussed below. For example, the balloons may be filled to different volumes, including leaving one or more of the balloons completely unfilled (i.e., empty) to accommodate different bladder sizes and shapes. A stopcock and pumping mechanism (not shown) positioned between the fluid source and the second end of each tube may be used to control the flow of fluid into and/or out of the interior region of each balloon.

The medical device of FIG. 1 is configured to be inserted through the urethra into the bladder of a patient in a collapsed configuration. In various embodiments, when the tiered balloons are in a collapsed configuration the medical device may have a profile (or diameter) less than 3.7 mm, preferably less than 2.8 mm, and more preferably less than or equal to 2.5 mm. In some embodiments, the medical device may be disposed within the lumen of an introducing element such as, for example, a cystoscope (not shown) for introduction through the patient's urethra. Once properly positioned within the bladder, each of the tiered balloons may be individually expanded by flowing fluid from the fluid source into the interior region of the balloon through its respective tube, such that each electrode disposed about the outer surface of the balloon may be placed into firm contact with a tissue of the bladder wall. Each balloon expands outward from the catheter towards the bladder wall. Because the internal dimensions of the bladder change along its length, each balloon may be expanded until the electrodes carried about the outer surface of the balloon are placed in contact with the tissues of the bladder wall. Given the substantially oval shape of the bladder depicted in FIG. 1, the central balloon (i.e., first tier balloon 20a) may be expanded to a greater extent than the balloons on either side of the central balloon (i.e., second tier balloons 20b), which are likewise expanded to a greater extent than the top and bottom balloons (i.e., third tier balloons 20c).

Although bladder volumes may vary depending, for example, on the age and size of the patient, the average bladder volume may be between 100 mL and 1500 mL and preferably approximately 400-600 ml. In one embodiment, each of the tiered balloons includes a maximum volume of approximately 200 ml when it the expanded configuration. Thus, the five balloons shown in FIG. 1 have a total maximum volume of approximately 1000 ml when in the fully expanded configuration. Because this volume exceeds the average bladder volume of 400-600 ml, the likelihood of any of the balloons rupturing due to overfilling is reduced. In another embodiment, the balloons of each tier include incrementally different maximum volumes depending on their location about the distal end of the catheter, and therefore their position within the bladder. For example, the first tier balloon may include a maximum volume that exceeds the volume second tier balloons, which likewise include maximum volumes that exceed the volumes of the third tier balloons. By way of non-limiting example, the first tier balloon may include a maximum volume of approximately 200 ml, the second tier balloons may include a maximum volume of approximately 150 ml and the third tier balloons may include a maximum volume of approximately 100 ml. In certain embodiments, the maximum volume of a second tier balloon may be at least 5% to 50% greater than the volume of a third tier balloon, and the maximum volume of a first tier balloon may be at least 5% to 50% greater than the volume of a second tier balloon. In other embodiments, the maximum volume of a second tier balloon may be at least 100% greater than the volume of a third tier balloon, and the maximum volume of a first tier balloon may be at least 100% greater than the volume of a second tier balloon. As will be understood by those in the art, providing balloons with incrementally different volumes depending on their location along the distal end of the catheter reduces the profile (i.e., diameter) of the tiered balloon catheter when in the collapsed configuration, thereby providing less invasive introduction through the urethra and further limiting the likelihood of a balloon rupturing due to overexpansion.

Aberrant electrical activity may manifest in different tissue regions of the bladder wall at different bladder volumes. For example, a specific tissue region of the bladder wall may exhibit aberrant electrical activity at one bladder volume, while another tissue region may exhibit aberrant electrical activity at another (e.g., higher or lower) bladder volume. A beneficial feature of the individually expandable tiered balloons may be their ability to map the bladder wall at a variety of different bladder volumes. In one embodiment, the bladder may be expanded to various volumes by introducing a fluid into the bladder through an additional tube 15 (see FIG. 2) that traverses at least a portion of the catheter lumen. Somewhat analogous to the tubes that fluidly connected each balloon to the fluid source, the second end of the additional tube is connected to a fluid source and the first end of the tube empties into the bladder. By way of non-limiting example, fluid may be introduced into the bladder such that the bladder expands to 25 percent of its maximum volume. Each of the tiered balloons may then be individually expanded outward from the catheter such that the electrodes carried about the outer surface of each balloon are placed in contact with the tissues of the bladder wall. The bladder wall may then be mapped (as discussed below) to detect one or more tissue regions exhibiting aberrant electrical activity. Additional fluid may then be introduced such that the bladder expands to 50 percent of its maximum volume. Each of the tiered balloons may then be individually expanded to maintain contact between the electrodes and the tissues of the bladder wall. The bladder wall may then be mapped again. This process may be repeated by expanding the bladder to 75 percent and 100 percent of its maximum volume. After the bladder has been mapped at each bladder volume, the tissue region(s) exhibiting aberrant electrical activity may then be ablated (as discussed below). In one embodiment, the identified tissue region(s) may be ablated as they are discovered at that bladder volume. Alternatively, the tissue region(s) identified at each bladder volume may be ablated once the bladder has been expanded to 100 percent of its maximum volume. It should be appreciated that fewer than all of the balloons may be inflated in some applications. For example, the first and third tier balloons may be expanded while the second tier balloons remain unexpanded.

The tiered balloons may include a variety of shapes when in the expanded configuration, depending, for example, on the uninflated shape of the balloon and whether or not the balloons are formed from a compliant or a non-compliant material. For example, each of the balloons may include a flat-disk shape that includes two long parallel surfaces connected to by shorter semi-circular ends. When formed of a compliant material, the flat-disk shape may allow the balloon to expand radially outward from the central catheter in a substantially lateral direction while the two long surfaces remain substantially parallel to one another. The substantially parallel sides of the flat disk balloon configuration may allow each balloon to expand without substantially interfering with the expansion of an adjacent balloon(s). This configuration may also allow for more space between each balloon that may be filled with fluid to keep the bladder wall hydrated. Alternatively, each of the balloons may include a spheroidal shape, for example, an oblate spheroidal shape having an elliptical (i.e., oblong or oval) cross-section, wherein the balloon expands radially outward from the central catheter as well as substantially longitudinally along the catheter axis.

Each balloon of the tiered balloon catheter shown in FIG. 1 includes eight electrodes 40 disposed equidistantly about its outer surface. It should be appreciated, however, that the present disclosure is not limited to the number or arrangement of electrodes on the outer surface of each balloon. Any number of electrodes may be disposed about the outer surface of each balloon of the tiered balloon catheter. For example, there may be one, two, three, four, five, six, seven, eight, nine, ten, eleven, twelve, sixteen, twenty, twenty-four, or more electrodes. To ensure that the entire bladder is mapped in a uniform manner, the electrodes are beneficially disposed equidistantly about the outer surface of the balloon. For example, the electrodes may be arranged in a ring patter, spiral pattern or vertical pattern, as are known in the art. Electrodes may be arranged randomly or in an ordered fashion, for example they may be more densely distributed in the area around bladder neck and less densely distributed in the dome. Each of the electrodes disposed about the outer surface of each balloon may be coupled to an electrically conductive wire (not shown) for performing mapping and ablation functions, as discussed in detail below.

Figure 2:
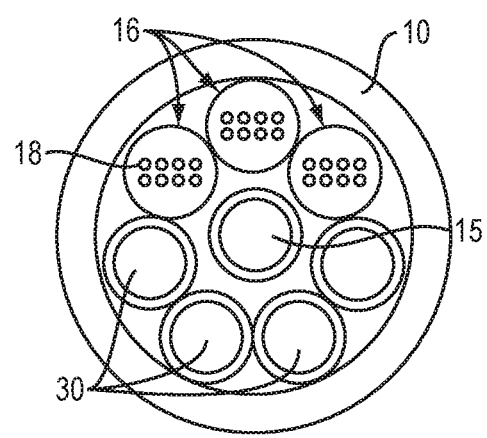
FIG. 2 is a cross-sectional view of the lumen that passes through the tiered balloon catheter depicted in FIG. 1.

FIG. 2 depicts a cross-sectional view of the catheter depicted in FIG. 1. Because the cross-sectional view is taken at a point just proximal to the first tier balloon 20a in FIG. 1, the catheter lumen 15 only depicts three of the five tubes 30 that fluidly connected each balloon with the fluid source. Sheaths 16 adjacent to (i.e., above) each of the tubes 30 include the eight electrically conducting wires 18 that are connected to each of the eight electrodes disposed about the outer surface of each balloon. An additional tube 15 for flowing fluid into the lumen of the bladder is also depicted.

Figure 3:
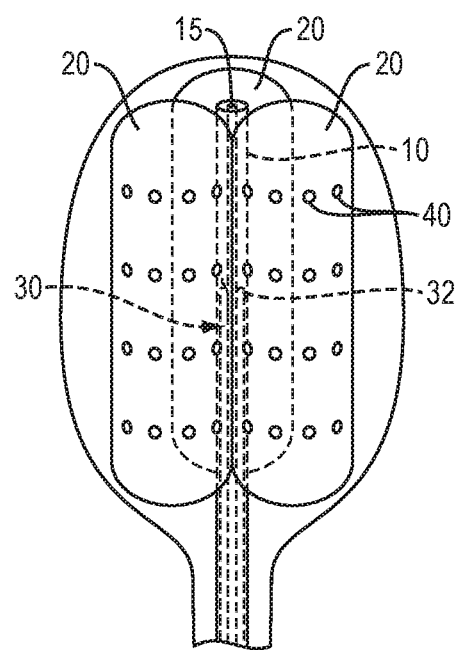
FIG. 3 is a side view of a non-compliant balloon catheter, according to another embodiment of the present disclosure.
Figure 4A:
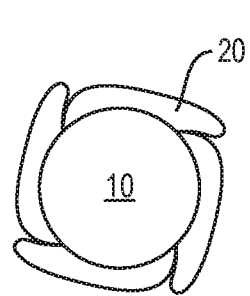
FIG. 4A is a cross-sectional view of the non-compliant balloon catheter of FIG. 3 in a collapsed configuration.
Figure 4B:
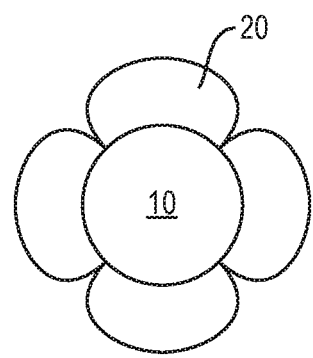
FIG. 4B is a cross-section view of the non-compliant balloon catheter of FIG. 3 in an expanded configuration.

FIG. 3 depicts a schematic side view of another embodiment of a medical device that includes three balloons 20 positioned around a longitudinal axis of the catheter 10, in particular, spaced at equal angles of rotation (120°) around the longitudinal axis of the catheter 10. FIGS. 4A and 4B depicts a schematic cross-sectional view of a device analogous to that of FIG. 3, except that four balloons 20 are positioned around a longitudinal axis of the catheter 10, in particular, spaced at equal angles of rotation (120°) around the longitudinal axis of the catheter 10. The balloons 20 in these embodiments may be formed from a compliant or non-compliant material. As noted above, a non-compliant balloon lacks elastic properties and can only assume one shape when in the expanded configuration. When the balloons 20 are formed from a non-compliant material and are in the deflated configuration, the balloons 20 may be folded around the central catheter 10 in an overlapping pattern to provide a small profile (or diameter) for insertion through the urethra into the bladder (FIG. 4A). Similar to the tiered balloons of FIG. 1, a plurality of tubes 30 traverse at least a portion of the catheter lumen 15, with the first end 32 of each tube fluidly connected to a different one of the plurality of balloons and the second end (not shown) of each tube connected to a fluid source (not shown). Each of the balloons are configured to move from a collapsed configuration (i.e., deflated) to an expanded (i.e., inflated) configuration independent of the other balloons by flowing a fluid from the fluid source into the balloon interior region through its respective tube (FIG. 4B). Although the embodiment depicted in FIG. 3 includes three balloons disposed at a distal end of the catheter, and the embodiment depicted in FIGS. 4A-B includes four balloons disposed at the distal end of the catheter, it will be appreciated that the present disclosure may include fewer or greater than three or four balloons. In the embodiment shown in FIG. 3, each of the non-compliant balloons further includes a series of electrodes 40 placed in a ring about the outer surface of the balloon 20. It should again be appreciated, however, that the present disclosure is not limited to the number or arrangement of electrodes on the outer surface of each balloon.

Once properly positioned within the bladder, each of the non-compliant balloons may be individually unfolded by flowing fluid from the fluid source into the interior region of the balloon through its respective tube. Each balloon may be unfolded until the electrodes disposed about the outer surface of the balloon are in contact with the tissues of the bladder wall, or until the balloon is at its maximum volume. As with the compliant tiered balloons of FIG. 1, the non-compliant balloons of FIGS. 3 and 4A-B beneficially may have a combined maximum volume that is capable of filling an average human bladder (e.g., 400-600 ml). For example, each of the three non-compliant balloons depicted in FIGS. 4A-B may have a maximum volume of approximately 130-200 ml when in the expanded configuration.

FIGS. 5A-B depict a schematic side view (FIG. 5A) and cross-sectional (FIG. 5B) view of another embodiment of a medical device in which a single balloon 20 is positioned asymmetrically (i.e., unevenly) about the distal end 14 of the catheter 10, partially encircling a longitudinal axis of the catheter 10, rather than completely encircling the same. Similar to the tiered balloons of FIG. 1, a tube 30 traverses a portion of the catheter lumen 15, with the first end of each tube fluidly connected to the interior region of the asymmetric balloon and the second end of each tube connected to a fluid source (not shown). The asymmetric balloon is configured to move from a collapsed configuration (i.e., deflated) to an expanded (i.e., inflated) configuration by flowing a fluid from the fluid source into the balloon interior region through the tube. Although the balloon 20 shown in FIGS. 5A-B extends around the longitudinal axis by an amount of about 180° in the embodiment shown, in various embodiments, the balloon 20 may extend around the longitudinal axis by an amount ranging, for example, from 90° to 270°, among other values. Although the embodiment depicted in FIGS. 5A-B includes a single balloon, it will be appreciated that the present disclosure may include multiple balloons distributed asymmetrically about the distal end of the catheter. The asymmetric balloon of FIG. 5A further includes a series of electrodes 40 placed in linear strips that run perpendicular to the longitudinal axis of the catheter 10. It should again be appreciated, however, that the present disclosure is not limited to the number or arrangement of electrodes on the outer surface of each balloon. The asymmetric design allows the balloon to conform to the shape of a portion of the bladder when in the expanded configuration, while also providing ample space for fluid to keep the bladder wall hydrated.

Once properly positioned within the bladder, the asymmetric balloon may be expanded by flowing fluid from the fluid source into the interior region of the balloon such that each electrode disposed about the outer surface of the asymmetric balloon may be placed into contact with a tissue of the bladder wall. The bladder may then be infused with saline, or other suitable electrically conductive fluid. The portion of the bladder in contact with the electrodes of the asymmetric balloon may then be mapped to identify tissue regions exhibiting aberrant electrical activity, followed by focal ablation of those tissue regions. The asymmetric balloon may then be at least partially collapsed by removing the fluid from the balloon interior region, and the device rotated within the bladder such that the collapsed asymmetric balloon faces a different portion of the bladder wall. The asymmetric balloon may then be re-expanded and the tissues of the bladder wall are mapped and, if necessary, ablated as described below. This procedure may be repeated as many times as necessary to map and ablate the entire bladder. This procedure may also be repeated at a variety of bladder volumes (e.g., 25 percent, 50 percent, 75 percent and 100 percent) as previously described.

FIG. 6 depicts a variation of the medical device of FIG. 1, in which each of the tired balloons 20*a-c* is configured to individually slide along the length of the catheter 10. In the embodiment shown, spacing elements 17, 17*a*, 17*b* (i.e., springs) are slidably disposed about the catheter to maintain a space between the balloons of each tier. The spaces may allow the bladder to be filled with fluid in a manner that more accurately simulates filling with urine. The top 17*a* and bottom 17*b* spacing elements may be attached to connecting guides (not shown) that allow the position of the tiered balloons to be adjusted along the length of the catheter. The balloons may be adjusted proximally or distally as desired to position the electrodes 40 disposed on the outer surface of each balloon in contact with the tissues of the bladder wall 6. For example, the connecting guide attached to the top spring may be pulled proximally (i.e., toward the bladder neck) to adjust the balloons proximally, while the connecting guide attached to the bottom spring may be pushed distally (i.e., toward the bladder dome) to adjust the balloons distally.

FIG. 7 depicts a schematic side view of another embodiment of a medical device in which the balloon 20 is configured to move from a collapsed configuration to an expanded configuration by flowing a fluid into the balloon interior region. However, the balloon depicted in FIG. 7 is formed from a porous material that allows the fluid to continuously seep through the wall of the balloon to hydrate the tissues of the bladder wall. As shown by the magnified view of FIG. 7, the porous material 25 may be distributed evenly throughout the surface of the balloon 20 such that the bladder is evenly hydrated. Although the balloon catheter depicted in FIG. 7 includes a single bladder-shaped balloon with one main cavity that is filled with saline, the porous balloon surface may also be incorporated into the tiered balloons of FIGS. 1 and 2, the longitudinal balloons of FIGS. 3, 4A and 4B and/or the asymmetrical balloon of FIG. 5A-B. Electrodes 40 may be disposed about the outer surface 22 of the balloon in a variety of patterns. For example, the electrodes may include separate splines of electrodes (e.g., with eight electrodes per spline, among other possibilities). The electrodes may be placed in a spiral design (e.g., one comprising of 64 electrodes, among other possibilities) attached to a wire that may be wound around the outer surface of the balloon. The electrodes may also include a series of separate electrode rings arranged about the outer surface of the balloon, with fewer electrodes placed on the rings that encircle the narrower portions of the balloon (i.e., top and bottom) and more electrodes placed on the rings that encircle the wider (i.e., middle) portions of the balloon.

Figure 9:
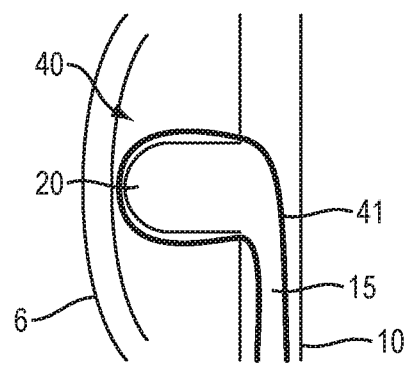
FIG. 9 is a side view of a ring electrode, according to another embodiment of the present disclosure.
Figure 10:
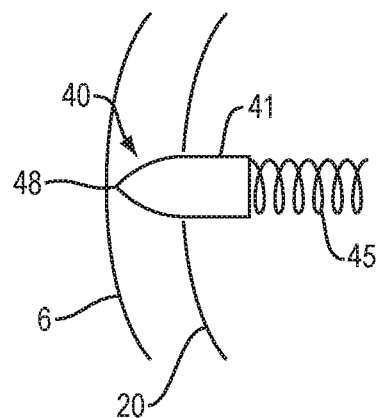
FIG. 10 is a side view of a plunge electrode, according to another embodiment of the present disclosure.
Figure 11:
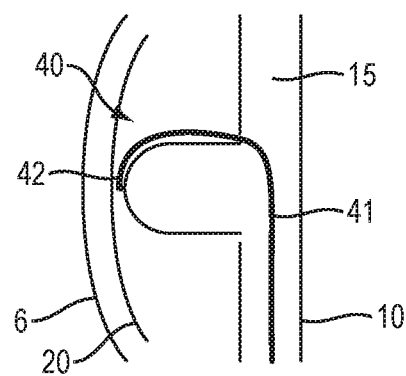
FIG. 11 is a side view of a single end electrode, according to yet another embodiment of the present disclosure.

The surface of the balloons described herein may include a variety of electrode designs for mapping and ablating the tissues of the bladder wall. Referring to FIG. 8, in one embodiment the electrode 40 may be an exposed electrode that includes a wire 41 that passes through small holes in the balloon 20 to form a loop 42 that may be exposed to the outside of the balloon for contact with the bladder wall 6. The remaining wire may be formed into a shape memorized (e.g., heat trained) coil within the balloon interior. The wire can uncoil and recoil as the balloon moves between the expanded and collapsed configurations. FIG. 9 depicts another variation of an electrode 40, which includes a wire 41 in the shape of a coiled ring that wraps around the external surface of the balloon 20 and feeds directly into the lumen 15 of the catheter. Although the balloon 20 shown is axially asymmetric (i.e., on one side of the catheter 10), in other embodiments the balloon is axially symmetric. This design eliminates the need for the wire to pass through small holes in the balloon surface. Slack provided to the portion of the wire 41 within the lumen 15 of the catheter 10 allows the electrode to uncoil and recoil as the balloon moves between the expanded and collapsed configurations. Referring to FIG. 10, in yet another embodiment, the electrode 40 may be a "plunge electrode" that includes a wire 41 formed in the shape of a heat trained coil 45 within the balloon interior that leads to a single point 48 that plugs a small hole in the balloon. The pointed end of the electrode extends beyond the outer surface of the balloon 20 to contact (i.e., plunge into) the tissues of the bladder wall (e.g., by forming a pressure indentation in the bladder wall or penetrating the bladder wall), thereby maintaining contact with the bladder wall 6. Referring to FIG. 11, in another embodiment analogous to that of FIG. 9, the electrode 40 may include a single wire 41 that curls around one-half of the outer surface of the balloon 20 such that the distal end 42 of the wire 41 is positioned at a middle portion of the balloon. The wire 41 feeds out of the lumen 15 of the catheter 10 and may be trained in a half-circle formation. As the balloon moves between the expanded and collapsed configurations, the wire has sufficient space to freely move within the lumen of the catheter. The electrode at the end of the wire may, for example, rest laterally against the outer surface of the balloon, or be shaped as a plunge-type electrode that pushes against or penetrates a tissue of the bladder wall 6.

The balloons described herein may include a combination of elastomeric and semi to non-compliant materials. For example, balloon can include one or more thermoplastics and/or thermosets. Examples of thermoplastics include polyolefins; polyamides (e.g., nylon, such as nylon 12, nylon 11, nylon 6/12, nylon 6, nylon 66); polyesters (e.g., polyethylene terephthalate (PET), polybutylene terephthalate (PBT), polyethylene naphthalate (PEN), polytrimethylene terephthalate (PTT)); polyethers; polyurethanes; polyvinyls; polyacrylics; fluoropolymers; copolymers and block copolymers thereof, such as block copolymers of polyether and polyamide (e.g., PEBAX®); and mixtures thereof. Examples of thermosets include elastomers (e.g., EPDM), epichlorohydrin, polyureas, nitrile butadiene elastomers and silicones. Other examples of thermosets include epoxies and isocyanates. Biocompatible thermosets may also be used. Biocompatible thermosets include, for example, biodegradable polycaprolactone, poly(dimethylsiloxane) containing polyurethanes and ureas and polysiloxanes. Ultraviolet curable polymers, such as polyimides, can also be used. Other examples of polymers that can be used in balloons include polyethylenes, polyethylene ionomers, polyethylene copolymers, polyetheretherketone (PEEK), thermoplastic polyester elastomers (e.g., Hytrel®), and combinations thereof. The balloon may include multiple layers provided by, for example, co-extrusion. Other polymers are described, for example, in U.S. Pat. Pub. No. 2005/0043679, filed on Aug. 21, 2003, entitled "Medical Balloons," which is incorporated herein by reference.

Mapping electrode for use with medical ablation systems are described, for example, in U.S. Patent Publication Nos. 2008/0249518 and 2002/0177765, all of which are hereby incorporated by reference in their entirety. As mapping electrodes, the wire connected to each electrode may be electrically coupled to the input of an electrical activity processing system (not shown), such as, for example, an electromyograph. Each electrode may be assigned an electrode location and an electrode channel within the electrical activity processing system. The electrical activity processing system may be configured to detect the intrinsic electrical activity of the cells comprising the tissue region in contact with each electrode. The electrical activity processing system may then use the intrinsic electrical activity detected from each of the electrodes to provide a map of electrical activity throughout a given tissue region or organ. Based on this map, specific tissue regions exhibiting aberrant electrical activity as compared to the surrounding tissues may be identified. For example, the aberrant electrical activity may manifest as a region of elevated electrical activity compared to the surrounding (normal) tissue.

For use as ablation electrodes, each wire may also be electrically coupled to an energy source (not shown) configured to selectively deliver ablation energy its respective electrode. For example, once a tissue region exhibiting elevated electrical activity has been identified, the electrode(s) that detected the elevated electrical activity may be selectively energized to focally ablate that tissue region. Various energy sources may be used to deliver thermal energy to the target tissue, including, for example, radiofrequency (RF) energy, cryoablation energy, irreversible electroporation (IRE energy), microwave electromagnetic energy, laser energy, and/or acoustic energy, among others. For example, the energy source may include a conventional RF power supply that operates at a frequency in the range from 200 KHz to 1.25 MHz, with a conventional sinusoidal or non-sinusoidal wave form. Suitable power supplies are capable of supplying an ablation current at a relatively low voltage, typically below 150V (peak-to-peak), usually being from 50V to 100V. Simultaneous delivery of ablation energy to 64 electrodes will require a generator capable of delivering approximately 640 W. This wattage may be achieved by connecting multiple generators, e.g., 64 generators with a capacity of 20 W in series. Power supplies capable of operating within these ranges are available from commercial vendors, such as RadioTherapeutics of San Jose, Calif.

Once any one of medical devices disclosed herein are properly positioned within the bladder, the balloon or balloons may be inflated by introducing pressurized liquid or gas from a fluid source (not shown) into the interior region of the balloon body. The fluid or gas exerts pressure within the balloon body to urge the balloon from a collapsed configuration to an expanded configuration. The balloon may be expanded such that it conforms to inner dimensions of the bladder, thereby placing each of the electrodes on the outer surface of the balloon into contact with the tissues of the bladder wall. Continued exertion of pressure from the fluid or gas maintains the balloon body in the expanded configuration such that the electrodes remain in contact with the tissues of the bladder wall. In one embodiment, the fluid or gas may be continuously or intermittently circulated through the balloon body to maintain the balloon body in its expanded configuration. An electrically conductive fluid, such as saline, is then infused into the space between the outer surface of the balloon and the bladder wall.

With the balloon properly expanded within the bladder, the mapping function of each electrode may be activated to sense/detect the intrinsic electrical activity of the tissue region that it contacts. Once a tissue region of the bladder wall exhibiting elevated electrical activity has been identified, ablation energy may be selectively delivered from the energy source to the electrode(s) the sensed the elevated electrical activity. This focal delivery of ablation energy causes the electrically overactive cell(s) of the identified tissue region to be heated to the point of cell death, thereby creating scar tissue having reduced electrical activity.

The duration and/or intensity of the ablation energy may vary as necessary to achieve a satisfactory reduction of the elevated electrical activity. For example, ablation energy may be provided as a pulse, or series of pulses, of RF energy. The mapping function of the electrodes may then be re-established to determine if the identified tissue region continues to exhibit elevated electrical activity. In the event that the electrical activity within such sites remains elevated, the selected tissue region may be re-energized with ablation energy. This process may be repeated as necessary until the tissue region exhibits a desired level of electrical activity. The ability of the inflatable balloon and attached electrodes to repeatedly monitor and ablate regions of the bladder wall ensures that focal energy is delivered only to the target region, and without prolonging the duration or intensity of the energy. This targeted approach not only focuses the energy on the selected regions in need of ablation, but minimizes or eliminates unwanted and potentially harmful ablation of surrounding healthy/normal tissues.

While the tissue region that is identified and ablated may be in direct contact with an electrode, it should be appreciated that the target tissue may be in the general vicinity of an electrode. In this situation, one or more of the electrodes adjacent to the target tissue may be energized such that the zone of ablation energy reaches (i.e., overlaps with) the target tissue.

Once the mapping function of the electrodes has verified that the ablated tissue region no longer exhibits elevated electrical activity (as noted above, this process can be repeated for different catheter orientations and at different degrees of bladder expansion), the balloon may be returned to the collapsed configuration by removing the liquid or gas inflation medium from the interior region of the balloon body. The balloon may then retracted into the lumen of the catheter and withdrawn through the urethra.

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
   a catheter comprising a proximal end, a distal end, and a lumen extending therebetween;
   a plurality of disc-shaped balloons stacked along a longitudinal axis of the catheter proximate the distal end of the catheter, the plurality of disc-shaped balloons comprising a first balloon, a second balloon on either side of the first balloon, and a third balloon on either side of the stack of first and second balloons, wherein the first balloon has a greater maximum volume than each of the second balloons on either side of the first balloon, and wherein each of the second balloons have a greater maximum volume than each of the third balloons on either side of the stack of first and second balloons;
   a plurality of tubes traversing at least a portion of the catheter lumen, wherein a first end of each of the plurality of tubes is fluidly connected to a different one of the plurality of disc-shaped balloons;
   a plurality of electrodes carried about a surface of each of the plurality of disc-shaped balloons; and an additional tube traversing at least a portion of the catheter lumen, the additional tube configured to introduce a fluid into the human bladder.

2. The medical device of claim 1, wherein each of the plurality of disc-shaped balloons comprises a compliant polymer selected from the group consisting of silicone rubbers, polyurethanes, butyl rubbers, latexes, styrene-isobutylene-styrene block copolymers and EPDM, or a non-compliant polymer selected from PEBAX, PET, PEN, PBT, PEEK, Hytrel, polyurethane and nylon.

3. The medical device of claim 1, wherein each of the plurality of balloons is configured to move between a collapsed configuration and an expanded configuration.

4. The medical device of claim 1, wherein a second end of each of the plurality of tubes is in fluid communication with a fluid source, and wherein each of the plurality of disc-shaped balloons moves from a collapsed configuration to an expanded configuration by flowing a fluid from the fluid source into the lumen of each of the plurality of disc-shaped balloons.

5. The medical device of claim 1, wherein each of the plurality of electrodes is adapted to contact a wall of the body lumen when the plurality of disc-shaped balloons are in an expanded configuration.

6. The medical device of claim 1, wherein each of the plurality of disc-shaped balloons is slidable along the distal end of the catheter.

7. The medical device of claim 1, wherein each of the plurality of disc-shaped balloons is biased from an adjacent balloon by a spring disposed about the catheter.

8. The medical device of claim 1, wherein the plurality of disc-shaped balloons are positioned around a longitudinal axis of the catheter.

9. The medical device of claim 1, further comprising a plurality of conducting wires, wherein a first end of each of the plurality of conducting wires is electrically coupled to a different one of the plurality of electrodes.

10. The medical device of claim 9, wherein a second end of each of the plurality of conducting wires is electrically coupled to an ablation energy source.

11. The medical device of claim 9, wherein a second end of each of the plurality of conducting wires is electrically coupled to an electrical activity processing system.

12. The medical device of claim 1,
    wherein at least a portion of at least one of the plurality of balloons is fluid permeable.

13. The medical device of claim 1, wherein the plurality of disc-shaped balloons have a total maximum volume of approximately 1000 ml.

14. The medical device of claim 1, wherein the plurality of disc-shaped balloons are spaced along a longitudinal axis of the catheter.

15. The medical device of claim 1, wherein each of the plurality of disc-shaped balloons is expandable independent of the other balloons.

16. The medical device of claim 1, wherein the plurality of disc-shaped balloons are inflatable to each have substantially the same volume.

17. A medical device, comprising:
    a catheter comprising a proximal end, a distal end, and a lumen extending therebetween;
    a plurality of disc-shaped balloons stacked along a longitudinal axis of the catheter proximate the distal end of the catheter and including a central first tier balloon, a second tier balloon on either sides of the central first tier balloon, and a third tier balloon on either side of the stack of first and second tier balloons, wherein the first tier balloon has a greater maximum volume than each of the second tier balloons on either side of the first tier balloon, and wherein each of the second tier balloons have a greater maximum volume than each of the third tier balloons on either side of the stack of first and second tier balloons;
    a plurality of tubes traversing at least a portion of the catheter lumen, wherein a first end of each of the plurality of tubes is fluidly connected to a different one of the plurality of balloons;
    a plurality of electrodes carried about a surface of each of the plurality of balloons; and
    an additional tube traversing at least a portion of the catheter lumen, the additional tube configured to introduce a fluid into the human bladder.

18. The medical device of claim 17, wherein each of the plurality of disc-shaped balloons is expandable independent of the other balloons.

19. The medical device of claim 17, wherein the first tier balloon has a different maximum volume than the second tier balloons and the third tier balloons, the second tier balloons have a different maximum volume than the first tier balloon and the third tier balloons, and the third tier balloons have a different maximum volume than the first tier balloon and the second tier balloons.

20. A method, comprising:
- introducing the medical device of claim 1 into a body lumen;
- moving at least one of the plurality of disc-shaped balloons from a collapsed configuration to an expanded configuration such that the plurality of electrodes carried about the surface of the plurality of the disc-shaped balloons contact a tissue of the body lumen;
- measuring the electrical activity within the tissue of the body lumen in contact with each of the plurality of electrodes;
- identifying ones from the plurality of electrodes that detected an elevated electrical activity within the tissue of the body lumen; and
- applying electrical energy to the ones from the plurality of electrodes that identified elevated electrical activity.

\* \* \* \* \*